(12) United States Patent
Schnell et al.

(10) Patent No.: US 8,103,071 B2
(45) Date of Patent: Jan. 24, 2012

(54) MR-COMPATIBLE VIDEO SYSTEM

(75) Inventors: Wilfried Schnell, Forchheim (DE); Stefan Thesen, Dormitz (DE)

(73) Assignee: Siemens Aktiengesellschaft, Munich (DE)

( * ) Notice: Subject to any disclaimer, the term of this patent is extended or adjusted under 35 U.S.C. 154(b) by 861 days.

(21) Appl. No.: 12/217,035

(22) Filed: Jul. 1, 2008

(65) Prior Publication Data
US 2009/0010510 A1    Jan. 8, 2009

(30) Foreign Application Priority Data

Jul. 4, 2007  (DE) .................. 10 2007 030 972

(51) Int. Cl.
*G06K 9/00* (2006.01)
(52) U.S. Cl. ........................................ 382/128
(58) Field of Classification Search ............ 382/128
See application file for complete search history.

(56) References Cited

U.S. PATENT DOCUMENTS

| | | | |
|---|---|---|---|
| 5,412,419 A | | 5/1995 | Ziarati |
| 5,812,257 A | * | 9/1998 | Teitel et al. ............. 356/141.4 |
| 5,877,732 A | * | 3/1999 | Ziarati ............................ 345/8 |
| 6,307,589 B1 | * | 10/2001 | Maquire, Jr. .............. 348/333.03 |
| 6,369,952 B1 | * | 4/2002 | Rallison et al. ............... 359/630 |
| 2001/0028309 A1 | * | 10/2001 | Torch ............................ 340/575 |
| 2004/0263171 A1 | * | 12/2004 | Yamagata ..................... 324/318 |
| 2005/0007552 A1 | * | 1/2005 | Fergason et al. ............... 351/210 |
| 2005/0235422 A1 | | 10/2005 | Wallace |
| 2009/0018419 A1 | * | 1/2009 | Torch ............................ 600/318 |

FOREIGN PATENT DOCUMENTS

EP  1 541 966 A1  6/2005

OTHER PUBLICATIONS

Functional MRI, VisuaStim XGA, Resonance Technology, Inc. www.mrivideo.com, (Jun. 21, 2006).*
Resonance Technology Inc., Northridge, US; "CinemaVision"; pp. 1-2., Jun. 13, 2007.

* cited by examiner

*Primary Examiner* — Rodney Fuller

(57) ABSTRACT

In an MR-compatible video system, MR-compatible video eyeglasses are connected to a graphics unit. A position sensor arrangement is connected to the graphics unit to detect the position and/or orientation of the MR-compatible video eyeglasses and/or the position of the pupils of a user. The graphics unit comprises means for producing image signals for MR-compatible video eyeglasses depending on the position and/or orientation of the MR-compatible video eyeglasses and/or the position of the pupils of the user.

16 Claims, 2 Drawing Sheets

MR-COMPATIBLE VIDEO SYSTEM

CROSS REFERENCE TO RELATED APPLICATIONS

This application claims priority of German application No. 10 2007 030 972.6 filed Jul. 4, 2007, which is incorporated by reference herein in its entirety.

FIELD OF THE INVENTION

The invention relates to an MR-compatible video system with MR-compatible video eyeglasses.

BACKGROUND OF THE INVENTION

Magnetic resonance imaging (MR imaging) is used in medical diagnostics to create image data of a layer or an area from inside a human or animal body. In MR imaging a strong and uniform static magnetic field of 0.2 to 3 Tesla in size or greater is required. Such magnetic fields, in particular with high field strengths from 1 Tesla, are produced by superconducting magnets. Usually the superconducting magnet is of hollow cylindrical design, a cylindrical patient tunnel being embodied inside the hollow cylinder. Also arranged in the hollow cylindrical interior of the superconducting magnet are gradient coils for position encoding of the magnetic resonance signals and high frequency antennae for excitation and also for receiving the magnetic resonance signals. The numbers of modules required for MR imaging make the patient tunnel which is already not very large in diameter even narrower.

For image recording a patient is required to remain inside the tunnel-shaped interior of the magnet ideally without moving. Whilst recording magnetic resonance images a significant amount of cooperation is required from the patient and during the recording of images a high level of noise is produced from the switched gradient fields in interaction with the constant magnetic field which is an additional significant nuisance for the patient. In addition there is the risk that the patient becomes claustrophobic due to the narrow interior and because he is generally required to lie on his back in the magnetic resonance device. The unpleasant feelings experienced by the patient are additionally made worse if a special head antenna is used for head examinations which surrounds the patient's head relatively tightly even in the field of vision. In the worst case scenario, especially during long examinations of half an hour or more, the examination has to be interrupted.

The closing-in situation experienced by the patient due to this head antenna is improved by the use of a double mirror which guides the patient's eyes in the direction of his feet. This gives a feeling of openness. The optical trick is certainly a little strange because the patient looks upward and then sees his feet.

From U.S. Pat. No. 5,412,419 an audio and video system is known, which can be used in an MR device without interference. With this system it is possible to divert the patient's attention during the image recording with an entertainment program.

Furthermore an audio visual headset from the company Resonance Technology Inc. in Northridge, USA, is on the market that includes MR-compatible headphones and MR-compatible eyeglasses. Here the entire arrangement of headphones and video eyeglasses is so compact that it can even be used inside a head antenna. The disadvantage exists here that the patient is disturbed by the video sequences that appear on the display. He may feel additionally insecure because he can no longer see anything that is going on outside.

SUMMARY OF THE INVENTION

The object of the invention is to specify an MR-compatible video system with MR-compatible video eyeglasses which removes the disadvantages of the prior art.

The object stated above is achieved by the features of the claims. According to this, provision is made in an MR-compatible video system with MR-compatible video eyeglasses for the MR-compatible video eyeglasses to be connected to a graphics unit, for a position sensor for detecting a position and/or an orientation of the MR-compatible video eyeglasses and/or the position of the pupils of a user to be connected to the graphics unit, and for the graphics unit to comprise means for generating image signals for the MR-compatible video eyeglasses depending on the position and/or orientation of the MR-compatible video eyeglasses and/or the position of the pupils of the user. During the examination, the patient is thus no longer completely shut off from the environment but he can actively influence the images offered to him. The patient then obtains the impression that he is not so enclosed. Methods for generating images depending on a position are known sufficiently in the field of virtual reality.

In an advantageous embodiment, the image signals depict an examination room, a magnetic resonance device located in the examination room being depicted transparently. Thus, the magnetic resonance device in which the patient is positioned for his examination is virtually no longer present. He obtains an unrestricted view of the room in which he is at the time.

A little closer to reality is a further embodiment in which the image signals depict an examination room, a magnetic resonance device located in the examination room being depicted semi-transparently. The patient thus obtains a feeling of the magnetic resonance device surrounding him without significantly hindering the view in the examination room.

A further advantageous embodiment is distinguished by the fact that the position sensor comprises at least one pupil sensor. This means that without moving his head, the patient is offered a virtual image of the field of view produced thereby in accordance with the position of his pupils.

In a further advantageous embodiment the position sensor comprises at least one head position sensor. This means that head movements can also be used to control the images offered.

In a particularly advantageous embodiment the head position sensor is associated with a patient couch position detector. This means that a particularly simple realization for detecting the head position is produced thereby since, from the position of the patient couch, the position of the head in the longitudinal direction of the magnetic resonance device is also known.

A further particularly advantageous embodiment is distinguished by the fact that the head position sensor comprises magnetic field sensors. In this way, tilting of the head can be detected easily. The magnetic field required for determining the position and orientation is produced through a targeted or, in any case, necessary triggering of the gradient system to produce magnetic gradient fields. From the measurement signals, the position and orientation of the video eyeglasses is determined accordingly.

BRIEF DESCRIPTION OF THE DRAWINGS

An exemplary embodiment of the invention is explained in the following with the aid of two figures. These show.

DETAILED DESCRIPTION OF THE INVENTION

Figure 1:
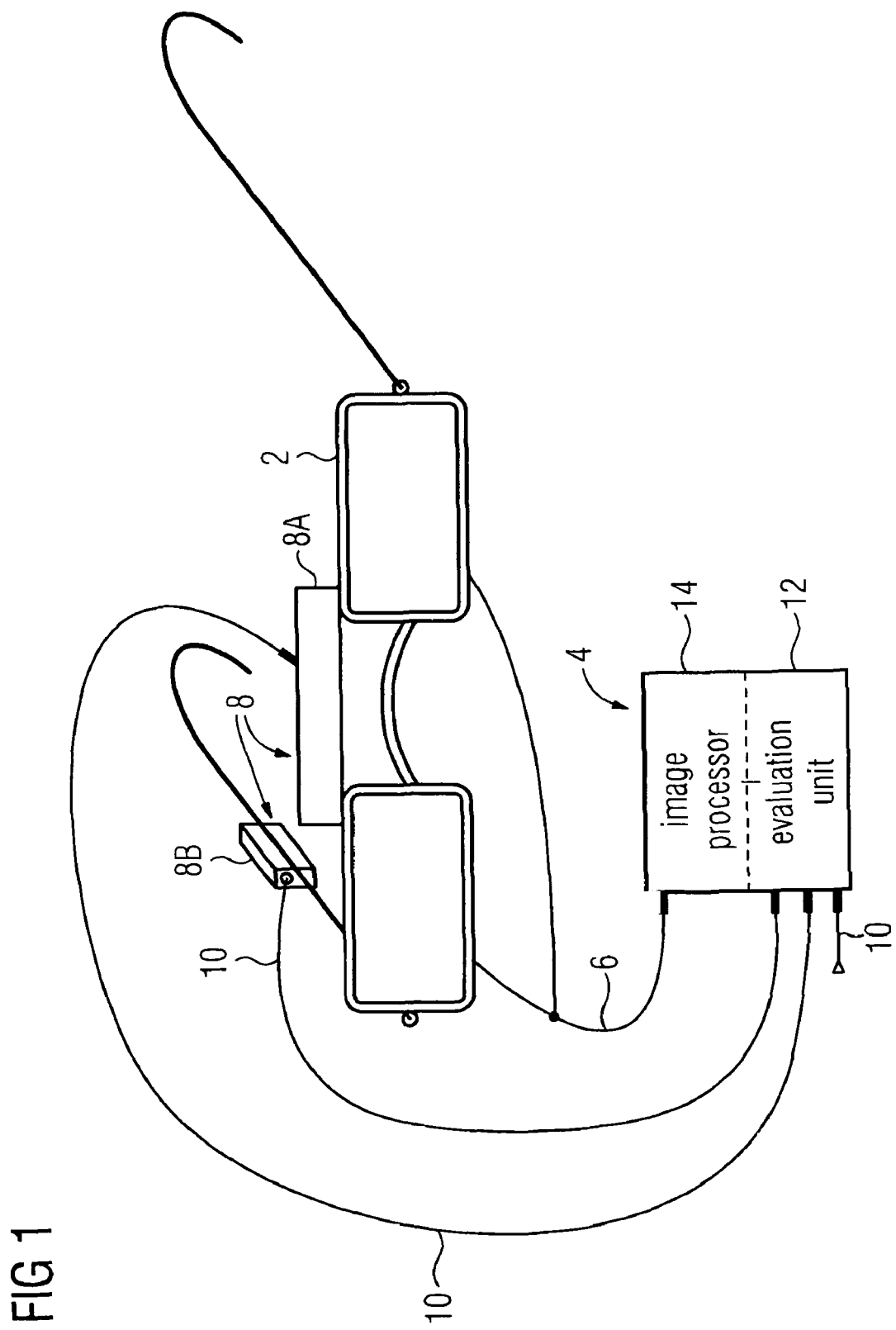
FIG. 1 a schematic representation of an MR-compatible video system.

The MR-compatible video system illustrated schematically in FIG. 1 comprises MR-compatible video eyeglasses 2. As already explained in the introduction, such video eyeglasses 2 are available on the market, for example from the company Resonance Technology Inc. in Northridge, USA. The MR-compatible design of the video eyeglasses 2 means that no interference of magnetic resonance imaging is created by the video eyeglasses 2 and that similarly, the magnetic fields and high-frequency fields used in the magnetic resonance device do not interfere with the operation of the video eyeglasses 2. The use of non-magnetic materials and electric shielding of the electric components are significant measures for ensuring MR-compatibility.

The MR-compatible video eyeglasses 2 are connected to a graphics unit 4. The image signals are produced in the graphics unit 4, which are then fed to the MR-compatible eyeglasses 2 with the aid of an MR-compatible signal link 6. Both electrically shielded and optical embodiments are considered as MR-compatible signal links 6.

A position sensor arrangement 8 is attached to the MR-compatible video eyeglasses 2 which detects a position and/or an orientation of the MR-compatible video eyeglasses 2. The position and/or orientation signals picked up by the position sensor arrangement 8 are fed to the evaluation unit 12 associated with the graphics unit 4 by means of a signal link 10. This signal link 10 must also be embodied as MR-compatible as it runs partially within and in the vicinity of the magnetic resonance device.

The position sensor arrangement 8 comprises a pupil sensor 8A which detects the position of the pupils of the video eyeglass user 2 or of the patient to be examined. Furthermore the position sensor arrangement 8 comprises a head position sensor 8B which detects the position and the tilt of the head. The field of view of the user is then assessed in the evaluation unit 12 from the position of the pupils and the position and tilt of the head using known methods from the field of virtual reality and fed to an image processor 14 associated with the graphics unit 4 for producing corresponding image views.

Figure 2:
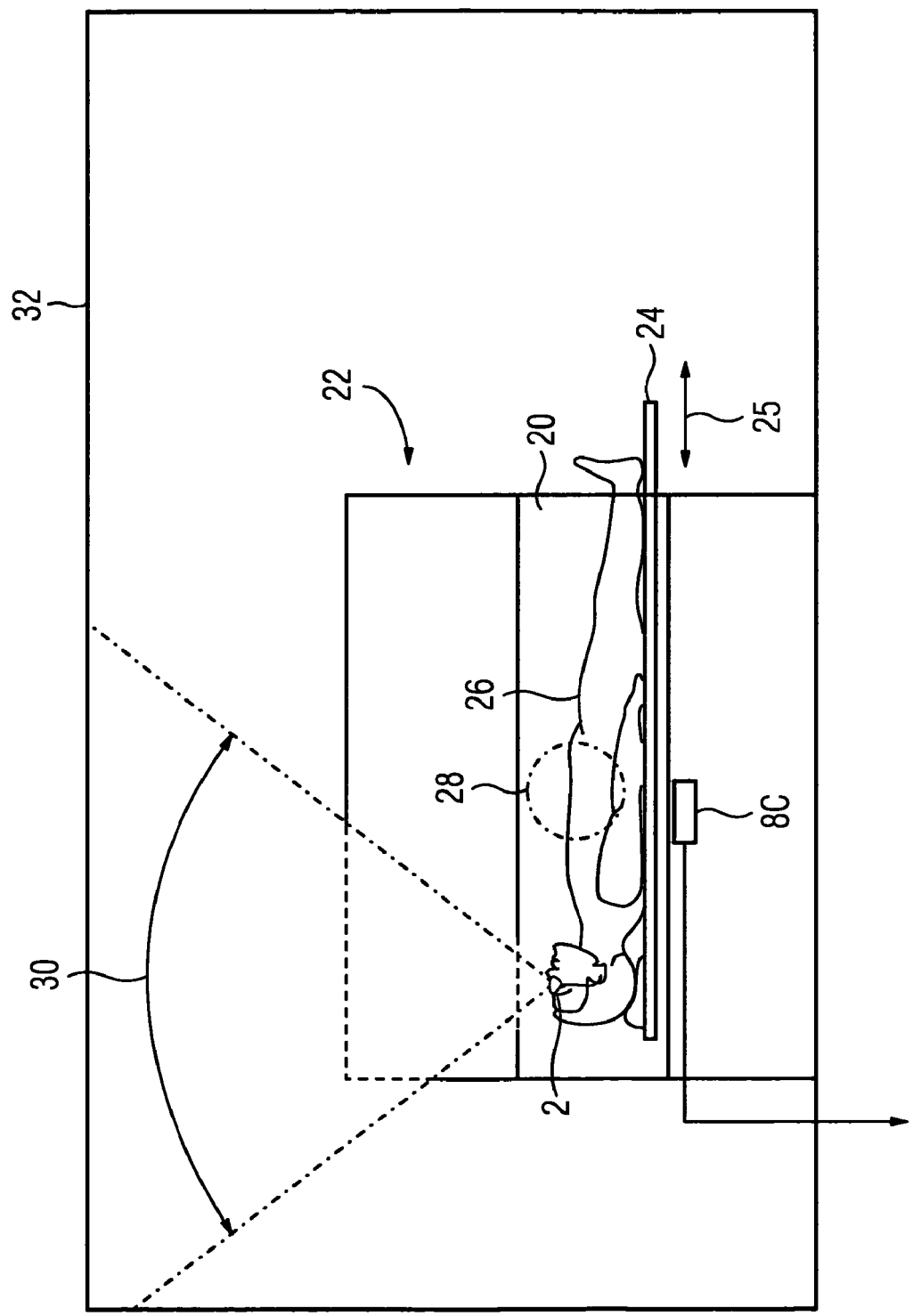
FIG. 2 a schematic representation of the MR-compatible video system for use in a diagnostic magnetic resonance device.

The function of the MR-compatible video system shall be explained with the aid of FIG. 2. A patient 26 is positioned on a patient couch 24 in the tunnel-shaped interior or patient tunnel 20 of a diagnostic magnetic resonance or MR device 22. The patient is moved with the patient couch 24 into the desired examination position in MR device 22 and this is depicted in FIG. 2 by a double-headed arrow 25. The MR device 22 has an essentially spherical-shaped imaging area 28 in which the region of the patient to be examined is located. The patient 26 is positioned such that image signals from the stomach region can be generated. So that the patient 26 does not feel disturbed by the narrowness of the tunnel 20, he wears MR-compatible video eyeglasses 2, which are equipped with the position sensor arrangement 8.

In FIG. 2 an alternative or also additionally employable embodiment of a position detector 8C of the video eyeglasses 2 is schematically illustrated. Use is made here of the fact that the at least approximate position of the video eyeglasses 2 in the magnetic resonance device is known indirectly from the known position of the patient couch 24. The position information of the patient couch 24 is fed by means of a further signal link 10 to the evaluation unit 12 in order to produce therefrom the image representation for the video eyeglasses 2 in the image processor 14. The field of view 30 produced from the position of the video eyeglasses 2 and/or the position of the pupils and/or from the position of the couch is illustrated in a side view in FIG. 2 by two dotted and dashed lines. The image representation for the video eyeglasses 2 now produces a view of the examination room 32 as would be produced from the direction of view of the patient 26. The magnetic resonance device 22 is then depicted in the field of vision 30 either fully transparently or even semi-transparently which is indicated by the dotted and dashed representation of the magnetic resonance device 22 in the field of vision 30.

The invention claimed is:

1. An MR-compatible video system, comprising:
  a graphics unit;
  an MR-compatible video eyeglasses connected to the graphics unit;
  a position sensor connected to the graphics unit that detects a position of the MR-compatible video eyeglasses based on a position of MR-compatible video eyeglasses, a position pupils of an individual wearing the MR-compatible video eyeglasses, and/or a position of a patient coach with respect to an MR device; and
  an image processor arranged in the graphics unit that generates an image signal for the MR-compatible video eyeglasses based on the position of the MR-compatible video eyeglasses, based on a position of MR-compatible video eyeglasses, a position pupils of an individual wearing the MR-compatible video eyeglasses, and/or a position of a patient coach with respect to an MR device.

2. The MR-compatible video system as claimed in claim 1, wherein the image signal depicts an examination room and a magnetic resonance device located in the examination room that is depicted transparently.

3. The MR-compatible video system as claimed in claim 1, wherein the image signal depict an examination room and a magnetic resonance device located in the examination room that is depicted semi-transparently.

4. The MR-compatible video system as claimed in claim 1, wherein the position sensor detects an orientation of the MR-compatible video eyeglasses.

5. The MR-compatible video system as claimed in claim 4, wherein the image signal is generated based on the position and the orientation of the MR-compatible video eyeglasses.

6. The MR-compatible video system as claimed in claim 1, wherein the position sensor comprises a pupil sensor that detects a position of a pupil of a user of the MR-compatible video eyeglasses.

7. The MR-compatible video system as claimed in claim 6, wherein the pupil sensor is attached to the MR-compatible video eyeglasses.

8. The MR-compatible video system as claimed in claim 6, wherein the image signal is generated based on the position of the pupil of the user.

9. The MR-compatible video system as claimed in claim 1, wherein the position sensor comprises a head position sensor that detects a position and a tilt of a head of the user of the MR-compatible video eyeglasses.

10. The MR-compatible video system as claimed in claim 9, wherein the head position sensor is attached to the MR-compatible video eyeglasses.

11. The MR-compatible video system as claimed in claim 9, wherein the head position sensor comprises a magnetic field sensor.

12. The MR-compatible video system as claimed in claim 1, wherein the image signal is generated based on the position of the pupil of the user and the position and the tilt of the head of the user.

13. The MR-compatible video system as claimed in claim 1, wherein the position sensor is connected to the patient couch position detector that detects a position of the patient couch.

14. The MR-compatible video system as claimed in claim 13, wherein the position of the head of the user of the MR-compatible video eyeglasses is determined based on the position of the patient couch.

15. An MR-compatible video system, comprising:
a graphics unit;
an MR-compatible video eyeglasses connected to the graphics unit;
a position sensor connected to the graphics unit and a patient couch that detects a position of the patient couch with respect to an MR device; and
an image processor arranged in the graphics unit that generates an image signal for the MR-compatible video eyeglasses based on the position of the pupil of the user of the MR-compatible video eyeglasses.

16. A method for generating an image signal for an MR-compatible video eyeglasses to be worn by a patient during an MRI examination, comprising:
detecting a position of the MR-compatible video eyeglasses based on a position of MR-compatible video eyeglasses, a position pupils of an individual wearing the MR-compatible video eyeglasses, and/or a position of a patient coach with respect to an MR device; and
generating the image signal based on the position of the MR-compatible video eyeglasses.

\* \* \* \* \*